United States Patent
Lee et al.

(10) Patent No.: US 7,718,577 B2
(45) Date of Patent: May 18, 2010

(54) LINKER COMPOUND, SUBSTRATE COATED WITH THE COMPOUND, METHOD OF PRODUCING MICROARRAY USING THE COMPOUND AND MICROARRAY PRODUCED BY THE METHOD

(75) Inventors: In-ho Lee, Gyeonggi-do (KR); Bong-jin Moon, Gyeonggi-do (KR); Jun-hong Min, Gyeonggi-do (KR); Jang-seok Ma, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 773 days.

(21) Appl. No.: 11/266,710

(22) Filed: Nov. 3, 2005

(65) Prior Publication Data

US 2006/0263793 A1    Nov. 23, 2006

(30) Foreign Application Priority Data

Nov. 3, 2004   (KR)   ................... 10-2004-0088914

(51) Int. Cl.
*C40B 40/00*   (2006.01)
(52) U.S. Cl. ............................................. 506/13; 435/6
(58) Field of Classification Search ....................... None
See application file for complete search history.

(56) References Cited

FOREIGN PATENT DOCUMENTS

JP        10-259187 A    *    9/1998

* cited by examiner

*Primary Examiner*—Jeffrey S. Lundgren
(74) *Attorney, Agent, or Firm*—Cantor Colburn LLP

(57) ABSTRACT

A compound represented by formula (4), a substrate coated with the compound, a method of producing a microarray using the compound, and a microarray produced by the method are provided.

12 Claims, 1 Drawing Sheet

LINKER COMPOUND, SUBSTRATE COATED WITH THE COMPOUND, METHOD OF PRODUCING MICROARRAY USING THE COMPOUND AND MICROARRAY PRODUCED BY THE METHOD

CROSS-REFERENCE TO RELATED PATENT APPLICATION

This application claims the benefit of Korean Patent Application No. 10-2004-0088914, filed on Nov. 3, 2004, in the Korean Intellectual Property Office, the disclosure of which is incorporated herein in its entirety by reference.

BACKGROUND OF THE INVENTION

1. Field of the Invention

The present invention relates to a novel linker compound, a substrate coated with the compound, a method of producing a microarray using the compound, and a microarray produced by the method.

2. Description of the Related Art

In a microarray, certain molecules are immobilized within discrete known regions on a substrate. Examples of such a microarray include polynucleotide and protein microarrays. Such a microarray is made using a method of sequentially synthesizing a probe material on a substrate or a spotting method in which a previously-synthesized probe material is immobilized on an activated substrate.

In a spotting method, a microarray is made by coating a linker material (e.g. GAPS (gamma-aminopropyltriethoxy silane) and GAPDES (gamma-aminopropyldiethoxy silane), etc.) having a reactive functional group, for example, an amino group, on a substrate and reacting the functional group and a probe material to immobilize the probe material on the substrate, or by coating a linker material on a substrate, activating the linker material, for example, modifying the linker material using N-hydroxysuccinimide (NHS) into a high reactive material, and reacting a probe material having the reactive functional group such as an amino group. Examples of compounds conventionally used as the linker material include an alkylsilane having a carboxylic group and an alkyl sulfur compound having a carboxylic group. These compounds have a silicon or sulfur atom, and thus can bind to a $SiO_2$ or Au substrate, and have a carboxylic group, and thus can be easily activated.

According to the conventional technology, a linker material can react with a probe material after being coated on a substrate and activated. Thus, reaction efficiency is low and uniform activation cannot be achieved. In addition, a conventional linker material includes a hydrophobic portion such as an alkyl group. Thus, in a method in which signals generated from a reaction between a probe material and a target material on a microarray manufactured using the conventional linker material are measured and analyzed, the analysis efficiency is poor due to a strong signal generated from non-specific binding of the probe material to a background portion, i.e., a strong noise.

The inventors of the present invention made efforts to solve the problems of the conventional technology and found a compound having high reactivity to a probe material and strong binding force when it is coated on a substrate, and thus can be used to produce a microarray. Thus, the present invention has been completed.

SUMMARY OF THE INVENTION

The present invention provides a compound having high reactivity to a probe material and strong binding force when it is coated on a substrate.

The present invention also provides a method of preparing the compound.

The present invention also provides a substrate coated with the compound.

The present invention also provides a method of producing a microarray using the compound.

The present invention also provides a microarray produced by the method.

According to an aspect of the present invention, there is provided a compound represented by formula (4):

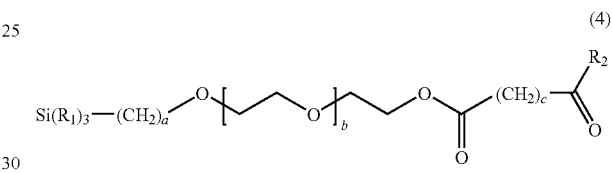

(4)

where each $R_1$ may be identical or different and is selected from a $C_1$-$C_2$ alkoxy group, a halogen and a formylalkyl group having a $C_1$-$C_3$ alkyl group, $R_2$ is

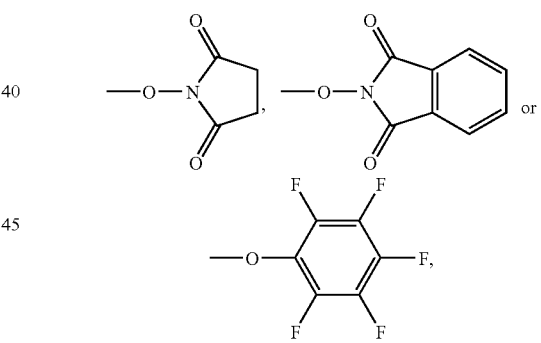

a is an integer from 3 to 18, b is an integer from 1 to 200, and c is an integer from 1 to 4.

According to another aspect of the present invention, there is provided a method of preparing a compound represented by formula (4):

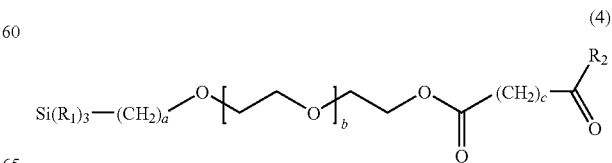

(4)

where each $R_1$ may be identical or different and is selected from a $C_1$-$C_2$ alkoxy group, a halogen and a formylalkyl group having a $C_1$-$C_3$ alkyl group, $R_2$ is

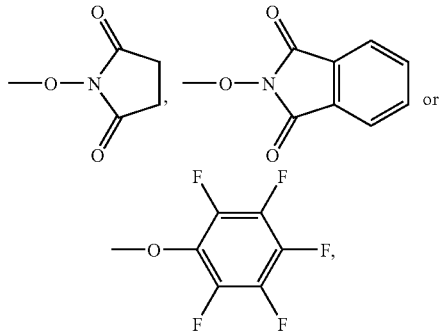

a is an integer from 3 to 18, b is an integer from 1 to 200, and c is an integer from 1 to 4, the method comprising:

reacting $C_4$-$C_{402}$ polyethyleneglycol with an allyl halide or an allylalkyl halide having a $C_1$-$C_{15}$ alkyl group in the presence of sodium hydride to obtain a compound represented by formula (1):

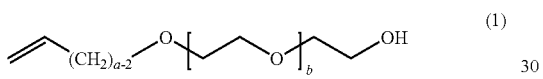

where a is an integer from 3 to 18 and b is an integer from 1 to 200;

reacting the resulting compound with a $C_3$-$C_6$ dicarboxylic anhydride in the presence of NaH or pyridine, along with a catalytic amount of dimethylaminopyridine (DMAP) to obtain a compound represented by formula (2):

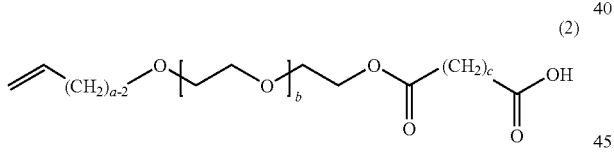

where a is an integer from 3 to 18, b is an integer from 1 to 200 and c is an integer from 1 to 4;

reacting the resulting compound with a compound represented by formula of $R_2H$, in which $R_2$ is

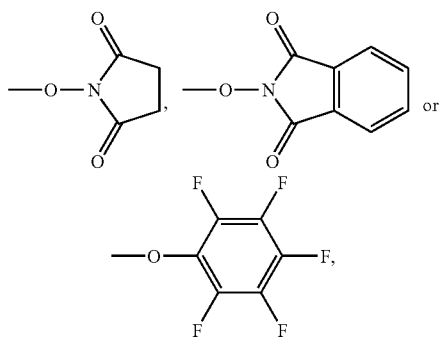

in the presence of N,N'-dicyclohexylcarbodiimide (DCC) to obtain a compound represented by formula (3):

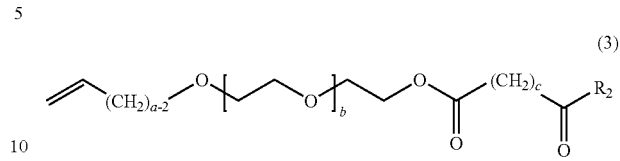

where a is an integer from 3 to 18, b is an integer from 1 to 200, c is an integer from 1 to4, and $R_2$ is

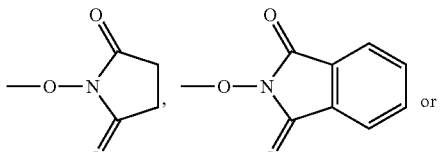

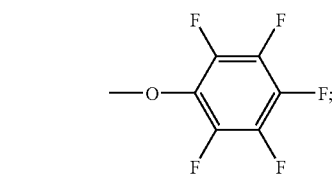

reacting the resulting compound with a compound represented by formula of $SiH(R_1)_3$, in which each $R_1$ may be identical or different and is selected from a $C_1$-$C_2$ alkoxy group, a halogen and a formylalkyl group having a $C_1$-$C_3$ alkyl group, in the presence of a Pt catalyst to obtain the compound represented by formula (4).

According to other aspects of the present invention, there are provided a substrate coated with the compound represented by formula (4), a method of producing a microarray using the compound represented by formula (4), and a microarray produced by the method.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
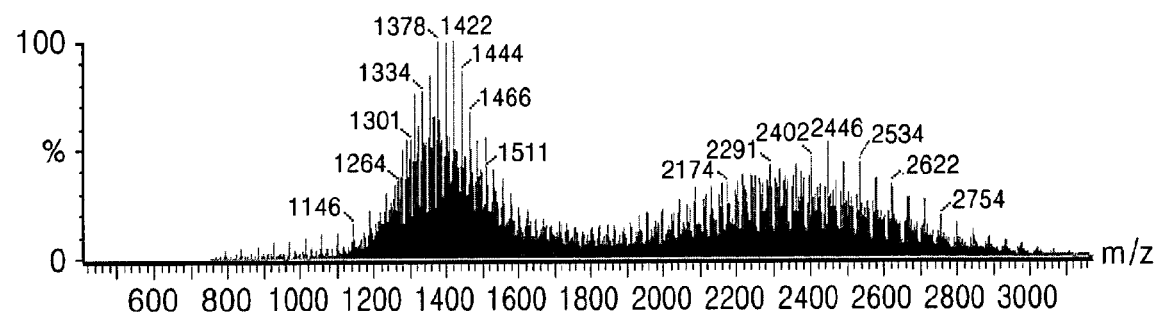
FIG. 1 is an ESI-Mass spectrum of a compound obtained from Example 1 of the present invention.

The present invention provides a compound represented by formula (4):

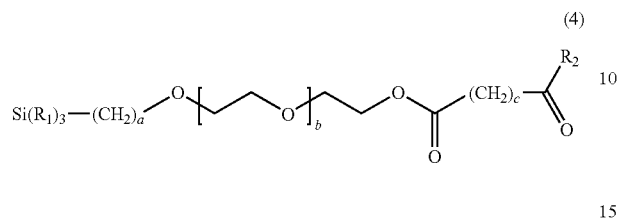

(4)

where $R_1$ may be identical to or different from each other and is selected from a $C_1$-$C_2$ alkoxy group, a halogen and a formylalkyl group having a $C_1$-$C_3$ alkyl group, $R_2$ is

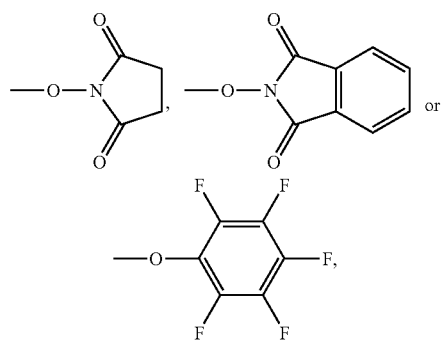

or a is an integer from 3 to 18, b is an integer from 1 to 200, and c is an integer from 1 to 4.

In the one embodiment of the compound represented by formula (4), $R_1$ is an ethoxy group, c is 2 or 3, and $R_2$ is

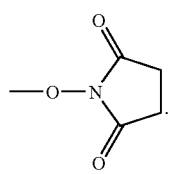

The compound includes a silane moiety capable of easily binding to a solid substrate, a hydrophilic PEG moiety increasing the hydrophilicity of molecule, and an activated functional moiety capable of causing a coupling reaction with a functional group such as an amino group. The solid substrate includes glass, a silicon wafer and a plastic substrate, but is not limited thereto. The solid substrate is not particularly limited in its shape and may be flat, a nanoparticle or a channel. The silane moiety has a structure represented by formula of $Si(R_1)_3$— in which $R_1$ may be identical to or different from each other and is selected from a $C_1$-$C_2$ alkoxy group, a halogen and a formylalkyl group having a $C_1$-$C_3$ alkyl group. The activated functional moiety includes a good leaving group that is substituted in the coupling reaction and a functional group for activating the good leaving group. The good leaving group is, for example,

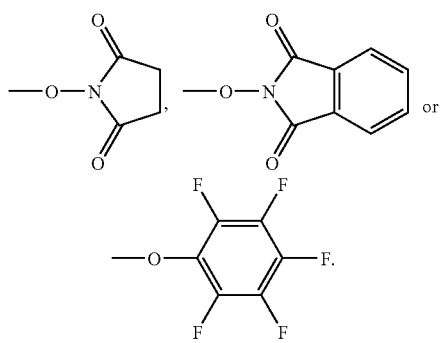

or

The functional group for activating the good leaving group is derived from dicarboxylate.

The compound of the present invention has the moiety capable of easily binding to a substrate and the good leaving group, and thus can be used as a linker material when a material is immobilized on a substrate. In this case, the PEG moiety is very hydrophilic, and thus can prevent a target material from non-specifically binding to a background portion when a probe material and the target material interact with each other. In addition, since the compound of the present invention includes the moiety capable of easily binding to a substrate and the good leaving group, the coating process of the compound on the substrate and the coupling process of a probe material can be continuously carried out using one compound.

The present invention also provides a method of preparing a compound represented by formula (4):

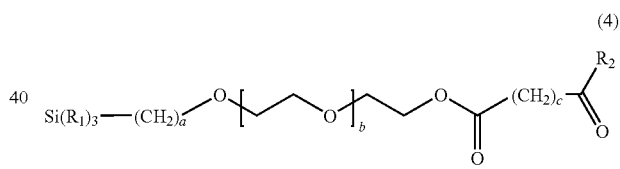

(4)

where $R_1$ may be identical to or different from each other and is selected from a $C_1$-$C_2$ alkoxy group, a halogen and a formylalkyl group having a $C_1$-$C_3$ alkyl group, $R_2$ is

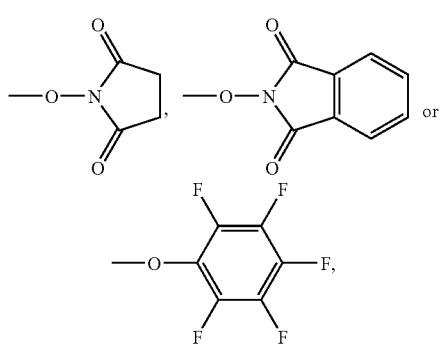

or a is an integer from 3 to 18, b is an integer from 1 to 200, and c is an integer from 1 to 4, the method including: reacting $C_4$-$C_{402}$ polyethyleneglycol with an allyl halide or an allylalkyl halide having a $C_1$-$C_{15}$ alkyl group in the presence of sodium hydride to obtain a compound represented by formula (1):

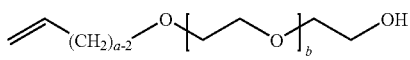
(1)

where a is an integer from 3 to 18 and b is an integer from 1 to 200; reacting the resulting compound with a $C_3$-$C_6$ dicarboxylic anhydride in the presence of NaH or pyridine, along with a catalytic amount of dimethylaminopyridine (DMAP) to obtain a compound represented by formula (2):

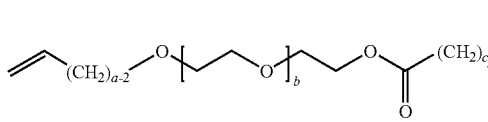
(2)

where a is an integer from 3 to 18, b is an integer from 1 to 200 and c is an integer from 1 to 4; reacting the resulting compound with a compound represented by formula of $R_2H$, in which $R_2$ is

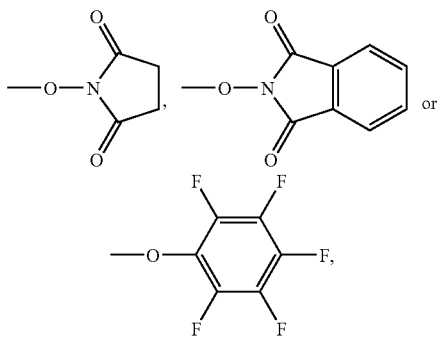

in the presence of N,N'-dicyclohexylcarbodiimide (DCC) to obtain a compound represented by formula (3):

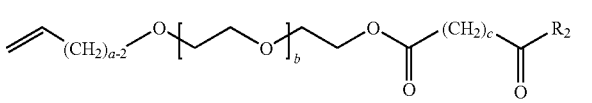
(3)

where a is an integer from 3 to 18, b is an integer from 1 to 200, c is an integer from 1 to 4, and $R_2$ is

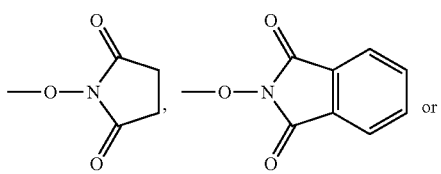

reacting the resulting compound with a compound represented by formula of $SiH(R_1)_3$, in which each $R_1$ may be identical or different and is selected from a $C_1$-$C_2$ alkoxy group, a halogen and a formylalkyl group having a $C_1$-$C_3$ alkyl group, in the presence of a Pt catalyst to obtain the compound represented by formula (4).

The compound represented by formula (4) can be synthesized, for example, according to the following procedure:

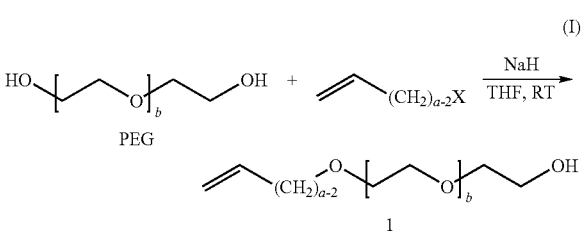
(I)

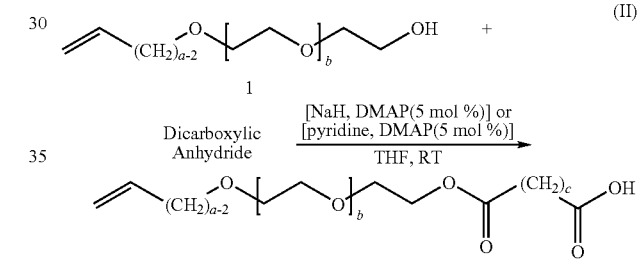
(II)

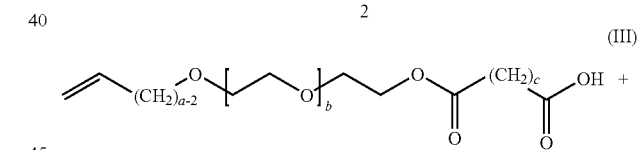
(III)

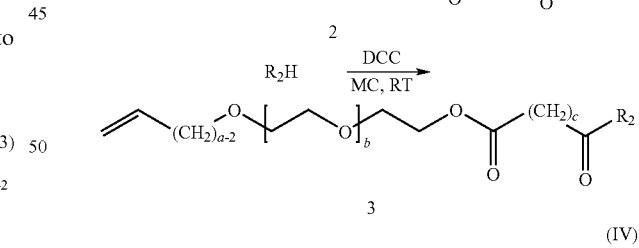
(IV)

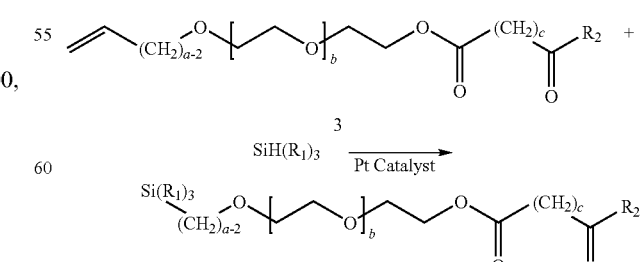

In the reaction (I), PEG and an allyl halide or an allylalkyl halide are reacted in the presence of NaH to obtain the compound represented by formula (1), which is an allylated or allyalkylated PEG. Preferably, PEG is a $C_4$-$C_{402}$ PEG, X is a halogen, a is an integer from 3 to 18, and b is an integer from 1 to 200. The reaction is carried out in an organic solvent such as THF, at a temperature of 0-30° C. and a pressure of about 1 atm for 3-24 hours. Preferably, the reaction is carried out in THF at room temperature for 3 hours.

In the reaction (II), the compound of represented by formula (1) is reacted with a dicarboxylic anhydride in the presence of NaH or pyridine, along with a catalytic amount of dimethylaminopyridine (DMAP, about 5 mol %) to obtain the compound represented by formula (2) which is an allylated or allylalkylated and dicarboxylated PEG. The dicarboxylic anhydride has 3 to 6 carbon atoms. The reaction is carried out in an organic solvent such as THF, at a temperature of 0-30° C. and a pressure of 1 atm for 3-24 hours. Preferably, the reaction is carried out in THF at room temperature for about 3 hours.

In the reaction (III), the compound represented by formula (2) is reacted with the compound represented by formula of $R_2H$ in the presence of DCC to obtain the compound represented by formula (3). In the compound represented by formula of $R_2H$, $R_2$ is

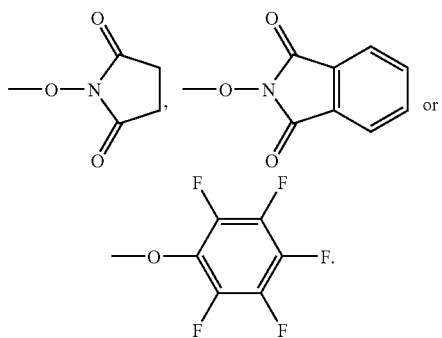

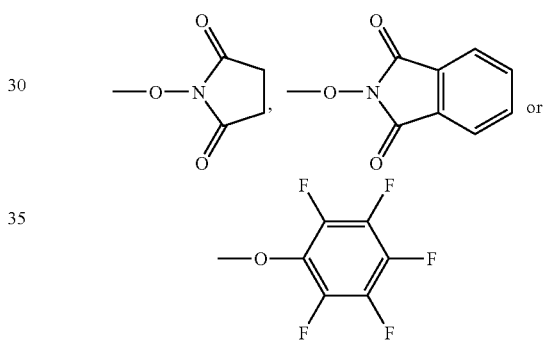

The reaction is carried out in an organic solvent such as methylene chloride (MC), at a temperature of 0-30° C. and a pressure of 1 atm for 1-4 hours. Preferably, the reaction is carried out in MC at room temperature for 2 hours.

In the reaction (IV), the compound represented by formula (3) is reacted with the compound represented by formula of $SiH(R_1)_3$ in the presence of a Pt catalyst to obtain the compound represented by formula (4). In the compound represented by formula (4), $R_1$ may be identical to or different from each other and is selected from a $C_1$-$C_2$ alkoxy group, a halogen and a formylalkyl group having a $C_1$-$C_3$ alkyl group. The reaction is carried out in an organic solvent such as toluene, THF, allylphenylether, etc., at a temperature of 60-100° C. and a pressure of 1 atm for 10-24 hours. Preferably, the reaction is carried out at a temperature of 60-70° C. for 16 hours without a solvent.

In an embodiment of the method, intermediates obtained in reactions (I), (II), (III) and (IV) are reacted in a state of a mixture with other by-products without purification.

The compound represented by formula (4) produced by the method is passed through an active carbon filter layer and a cellite filter layer to remove the catalyst and impurities and is concentrated. Alternatively, when b is 20 or greater, the compound may be purified by passing it through the above filters, adding the filtrate to diethylether or t-butylmethylether (MTBE), and filtering and drying the resulting precipitates.

The present invention also provides a method of producing a microarray, the method including: coating the compound represented by formula (4) on a solid substrate; and coupling the compound represented by formula (4) and a probe material to immobilize the probe material onto the substrate.

In an embodiment of the method, the solid substrate includes glass, a silicon wafer and a plastic substrate, but is not limited thereto. The solid substrate is not particularly limited in its shape, and may be flat, a nanoparticle and a channel. The coating process is generally performed in the production of a microarray and any coating method conventionally known in the art can be used in the present invention. For example, the coating can be achieved using a method selected from the group consisting of a self-assembled thin layer coating method, a spin coating method, a dipping method, a spraying method, a printing method and a Langmuir Blodget (LB) method. Those skilled in the art can perform the reaction using the above-described coating methods under appropriate conditions.

In the method, the coupling is achieved by reacting the good leaving group, for example, of the compound coated on the substrate with a functional group, for example, an amino group, of a probe material to substitute the good leaving group with the probe material. The probe material means a material immobilized onto a substrate, which can specifically bind to a target material. In the present invention, examples of the probe material include proteins, polynucleotides and polysaccharides, but are not limited thereto.

The present invention also provides a microarray produced by the method of producing a microarray. The microarray includes, for example, a protein microarray and a polynucleotide microarray.

The present invention also provides a solid substrate for a microarray, coated with the compound represented by formula (4).

The solid substrate includes glass, a silicon wafer and a plastic substrate, but is not limited thereto. The solid substrate is not particularly limited in its shape, and may be flat, a nanoparticle and a channel. The coating process is generally performed in the production of a microarray and any coating method conventionally known in the art can be used in the present invention. For example, the coating can be achieved using a method selected from the group consisting of a self-assembled thin layer coating method, a spin coating method, a dipping method, a spraying method, a printing method and an LB method. Those skilled in the art can perform the reaction using the above-described coating methods under appropriate conditions.

The present invention will now be described in greater detail with reference to the following examples. The following examples are for illustrative purposes only and are not intended to limit the scope of the invention.

EXAMPLES

Example 1

Synthesis of TES-PEG-succinate-NHS (8)

(poly(oxy-1,2-ethanediyl)-α-triethoxysilylpropyl-ω-[4-[(2,5-dioxo-1-pyrrolidinyl)oxy]-1,4-dioxobutoxy]ether)

1. Synthesis of allyl-PEG (5) (poly(ethylene glycol)-monoallyl ether)

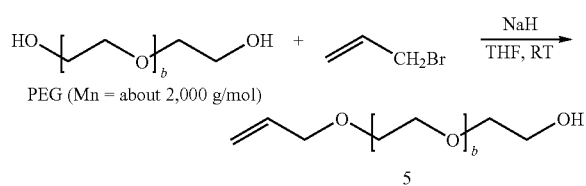

Under nitrogen atmosphere, NaH (800 mg, 20 mmol) and PEG (40 g, 20 mmol) (Mw=about 2,000) were charged into a flask, and then dry THF (200 mL) was added thereto at room temperature. The resulting slurry was stirred until hydrogen evolution was no longer observed (about 20 minutes). Next, allyl bromide (1.7 mL, 20 mmol) was added dropwise to the reaction mixture through a syringe. The obtained mixture was stirred at room temperature for 3 hours.

The resultant was centrifuged, and then the supernatant was decanted and solid residues were removed. The supernatant was dropped into t-butylmethyl ether (800 mL) at 0° C. to precipitate a polymer. The polymer was recovered by filtration and dried in vacuum to obtain 34 g (85%) of white solid. The NMR analysis result of the obtained white solid is as follows. It seems that the white solid is a 1:2:1 mixture of PEG:allyl-PEG:allyl-PEG-allyl.

1H NMR (300 MHz, CDCl$_3$): δ 5.9 (m, 1 H), 5.28 (dd, J1=14.1 Hz, J2=1.8 Hz, 1H), 5.18 (dd, J1=11.4 Hz, J2=1.8 Hz, 1H), 4.03 (d, J=5.7 Hz, 2H), 3.61 (m, —CH$_2$CH$_2$O—).

2. Synthesis of allyl-PEG-succinic acid (6)

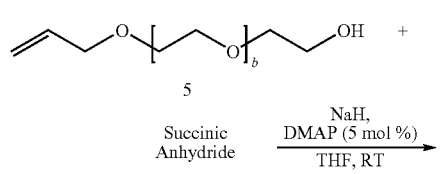

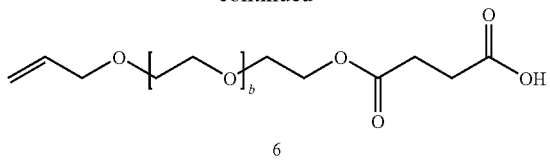

The polymer mixture (34 g, 17 mmol) obtained above (1), succinic anhydride (3.4 g, 34 mmol), NaH (1.36 g, 34 mmol), and dimethylaminopyridine (DMAP) (120 mg, 5 mol %) were charged into a flask under nitrogen atmosphere and dissolved in dry THF (150 mL) at room temperature. The mixture was stirred at room temperature for 3 hours, and then was subjected to ion exchange using an AMBERLITE™ IR-120 (+) resin. The resultant was filtered through a sintered glass filter and the filtrate was dropped to t-butylmethyl ether (500 ml) at 0° C. to precipitate a polymer. The polymer was recovered by filtration and dried in vacuum to obtain 32 g (95%) of white solid. The NMR analysis result of the obtained white solid is as follows. It seems that the white solid is a mixture of succinic acid-PEG-succinic acid:allyl-PEG-succinic acid:allyl-PEG-allyl.

1H-NMR (300 MHz, CDCl$_3$): δ 5.9 (m, 1H), 5.28 (dd, J1=14.1 Hz, J2=1.8 Hz, 1H), 5.18 (dd, J1=11.4 Hz, J2=1.8 Hz, 1H), 4.27 (t, J=4.5 Hz, 2H), 4.03 (d, J=5.7 Hz, 2H), 3.61 (m, —CH$_2$CH$_2$O—), 2.65 (m, 4H).

3. Synthesis of allyl-PEG-succinate-NHS (7)

(poly(oxy-1,2-ethanediyl)-α-allyl-ω-[4-[(2,5-dioxo-1-pyrrolidinyl)oxy]-1,4-dioxobutoxy]ether)

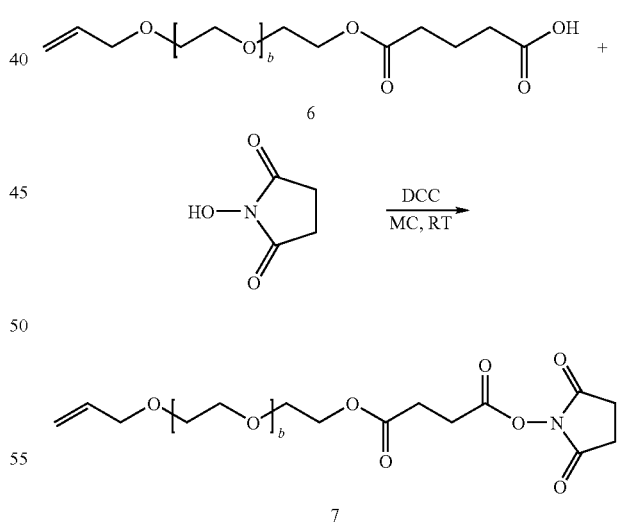

The polymer mixture (15 g, 7.5 mmol) obtained above (2) and N-hydroxysuccinimide (NHS) (1.73 g, 15 mmol) were dissolved in dry CH$_2$Cl$_2$ (150 ml) under nitrogen atmosphere at room temperature. A solution of N,N'-dicyclohexyl-carbodiimide (DCC) (3.1 g, 15 mmol) in dry methylene chloride (50 ml) was slowly added to the mixture through a syringe at 0° C. The obtained mixture was stirred at room temperature for 2 hours. The resultant was centrifuged, and then the supernatant was decanted and solid residues were removed. The supernatant was dropped into t-butylmethyl ether (500 mL) at 0° C. to precipitate a polymer. The polymer was recovered by filtration and dried in vacuum to obtain 14 g (93%) of white solid. The NMR analysis result of the obtained white solid is as follows. It seems that the white solid is a mixture of NHS-succinate-PEG-succinate-N HS:allyl-PEG-succinate-N HS (7) allyl-PEG-allyl.

1H-NMR (300 MHz, CDCl$_3$): δ 5.9 (m, 1 H), 5.28 (dd, J1=14.1 Hz, J2=1.8 Hz, 1H), 5.18 (dd, J1=11.4 Hz, J2=1.8 Hz, 1H), 4.27 (t, J=4.5 Hz, 2H), 4.03 (d, J=5.7 Hz, 2H), 3.61 (m, —CH$_2$CH$_2$O—), 2.96 (t, J=6.9 Hz, 2H), 2.84 (s, 4H), 2.78 (t, J=6.9 Hz, 2H).

4. Synthesis of TES-PEG-succinate-NHS (8)(poly(oxy-1,2-ethanediyl)-α-triethoxysilylpropyl-ω-[4-[(2,5-dioxo-1-pyrrolidinyl)oxy]-1,4-dioxobutoxy]ether)

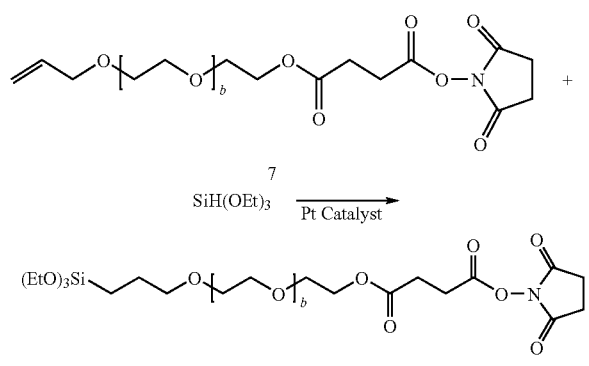

The polymer mixture (3 g, 1.5 mmol) obtained above (3) and a Pt oxide (4 mg, 0.1 mol %) were charged into a culture tube equipped with a screw cap and the culture tube was closed with a lid so as to have an opened screw cap and a septum. Allyl phenyl ether (2 g, 15 mmol) and triethoxysilane (TES) (2.98 g, 18.2 mmol) were sequentially added to the mixture through the septum using a syringe. The mixture was stirred at 60-70° C. for 16 hours. A brown mixture was filtered through a short pad of activated carbon and cellite. The filtrate was dropped into t-butylmethyl ether (100 mL) at 0° C. to precipitate a polymer. The polymer was recovered by filtration and dried in vacuum to obtain 2.5 g (83%) of gray solid. The NMR analysis result of the obtained gray solid is as follows. It seems that the gray solid is a 1:2:1 mixture of NHS-succinate-PEG-succinate-NHS:TES-propyl-PEG-succinate-NHS (8):TES-propyl-PEG-propyl-TES.

1H-NMR (300 MHz, CDCl$_3$): δ 4.27 (t, J=4.5 Hz, 2H), 3.61 (m, —CH$_2$CH$_2$O—), 2.96 (t, J=6.9 Hz, 2H), 2.84 (s, 4H), 2.78 (t, J=6.9 Hz, 2H), 1.7 (m, 2H), 1.2 (t, J=6.9 Hz, 9H), 0.62 (t, J=8.1 Hz, 2H).

The ESI-Mass analysis result of the obtained compound is illustrated in FIG. 1. The molecular weight of the compound (8) was about 2500, which was close to an estimated value of about 2420.

Example 2

Synthesis of Succinic Acid 2-{2-[2-(2-(3-triethoxysilylpropyloxy)-ethoxy)-ethoxy]-ethoxy}-ethyl 2,5-dioxo-pyrollidine-1-yl ester (12)

1. Synthesis of 2-{2-[2-(2-allyloxy-ethoxy)-ethoxy]-ethoxy}-ethanol (9)

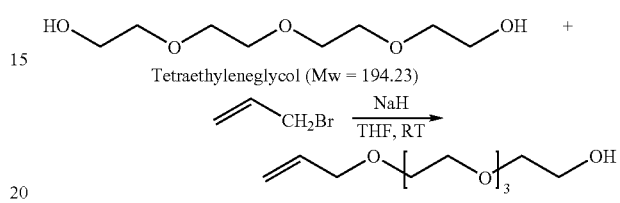

Under nitrogen atmosphere, NaH (1.2 g, 50 mmol) was charged into a flask, and then dry THF (15 mL) was added thereto and stirred at 0° C. for 15 minutes. Tetraethyleneglycol (10.7 g, 55 mmol) was added to the NaH mixture at 0° C. The mixture was stirred at room temperature for 1 hour. Next, the mixture was diluted with water (20 mL) and an organic material was extracted with methylene chloride (3×10 mL). The resulting organic layer was collected, dried on MgSO$_4$ and concentrated to obtain a crude product as yellow liquid. The crude product was purified with a column chromatography (Hex:EA=1:2 (10% MeOH)) to obtain the target product (3.8 g, 32%) in a colorless oily phase. The NMR analysis result of the obtained product is as follows.

1H NMR (300 MHz, CDCl$_3$): δ 5.9 (m, 1 H), 5.28 (dd, J1=14.1 Hz, J2=1.8 Hz 1H), 5.18 (dd, J1=11.4 Hz, J2=1.8 Hz, 1H), 4.03 (d, J=5.7 Hz, 2H), 3.61 (m, —CH$_2$CH$_2$O— 16H).

2. Synthesis of Succinic mono-(2-{2-[2-(2-allyloxy-ethoxy)-ethoxy]-ethoxy}-ethyl)ester (10)

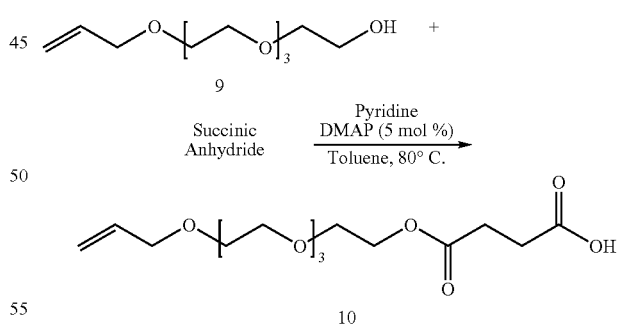

2-{2-[2-(2-allyloxy-ethoxy)-ethoxy]-ethoxy}-ethanol (9) (3.6 g, 15 mmol), succinic anhydride (1.8 g, 18 mmol), pyridine (1.22 mL, 15 mmol), dimethylaminopyridine (183 mg, 10 mol %), and dry toluene (5 mL) were charged into a screw cap culture tube. The mixture was stirred at 80° C. for 10 hours. Next, the reaction was stopped by adding 10% HCl (6 mL) and the reaction mixture was extracted with CH$_2$Cl$_2$ (3×10 mL). An organic layer was collected and dried on MgSO$_4$. AMBERLITE™ resin IR-120 (+) (2 g) was added and stirred to perform ion exchange. The resin was filtered off and the filtrate was concentrated to obtain yellow oil (5.2 g, 92%). The compound was used without further purification. The NMR analysis result of the compound is as follows.

1H NMR (300 MHz, CDCl$_3$): δ 5.9 (m, 1 H), 5.28 (dd, J1=14.1 Hz, J2=1.8 Hz 1H), 5.18 (dd, J1=11.4 Hz, J2=1.8 Hz, 1H), 4.03 (d, J=5.7 Hz, 2H), 3.61 (m, —CH$_2$CH$_2$O— 14H), 2.65 (s, 4H).

3. Synthesis of succinic 2-{2-[2-(2-allyloxy-ethoxy)-ethoxy]-ethoxy}-ethyl ester 2,5-dioxo-pyrollidine-1-yl ester (11)

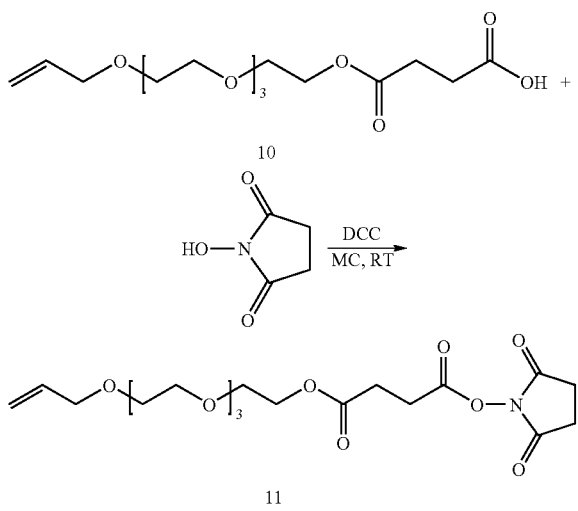

N-hydroxysuccin imide (1.58 g, 13.8 mmol) and succinic mono-(2-{2-[2-(2-allyloxy-ethoxy)-ethoxy]-ethoxy}-ethyl) ester (10) (4.6 g, 13.76 mmol) were dissolved in dry CH$_2$Cl$_2$ (10 mL) at room temperature. A solution of N,N'-dicyclohexylcarbodiimide (DCC) (2.84 g, 13.8 mmol) in dry CH$_2$Cl$_2$ (2 mL) was slowly added to the mixture at 0° C. The resulting mixture was stirred at room temperature for 2 hours. The solid residues in the reaction mixture were filtered through a sintered glass filter and removed and the filtrate was concentrated to obtain the target compound in a yellow oily phase (5.5 g, 93%). The compound was used without further purification. The NMR analysis result of the product is as follows.

1H-NMR (300 MHz, CDCl$_3$): δ 5.9 (m, 1 H), 5.28 (dd, J1=14.1 Hz, J2=1.8 Hz 1H), 5.18 (dd, J1=11.4 Hz, J2=1.8 Hz, 1 H), 4.03 (d, J=5.7 Hz, 2H), 3.61 (m, —CH$_2$CH$_2$O— 14H), 2.96 (t, J=6.9 Hz, 2H), 2.84 (s, 4H), 2.78 (t, J=6.9 Hz, 2H).

4. Synthesis of Succinic 2-{2-[2-(2-(3-triethoxysilylpropyl)-ethoxy)-ethoxy]-ethoxy}-ethyl ester 2,5-dioxo-pyrollidine-1-yl ester (12)

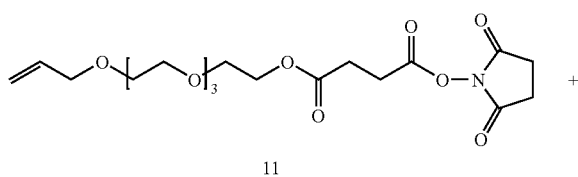

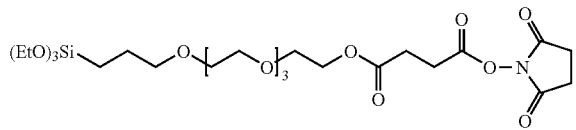

Succinic 2-{2-[2-(2-allyloxy-ethoxy)-ethoxy]-ethoxy}-ethyl ester 2,5-dioxo-pyrollidine-1-yl ester (11) (3 g, 6.9 mmol) was charged into a screw cap culture tube and the culture tube was closed with a lid so as to have a closed screw cap and a septum under nitrogen atmosphere. Triethoxysilane (2.3 g, 14 mmol) and Karstedt's catalyst (0.1 mL) were sequentially added to the mixture through the septum using a syringe. The mixture was stirred at 80° C. for 16 hours to obtain a brown solution. The brown solution was filtered through a short pad of activated carbon and cellite. The filtrate was concentrated to obtain the target compound in a yellow oily phase. The compound (3.1 g, 75%) was used without further purification.

1H-NMR (300 MHz, CDCl$_3$): δ 4.27 (t, J=4.5. Hz, 2H), 3.82 (m, 6H), 3.61 (m, —CH$_2$CH$_2$O— 14H), 3.43 (t, J=6.9 Hz, 2H), 2.96 (t, J=6.9 Hz, 2H), 2.84 (s, 4H), 2.78 (t, J=6.9 Hz, 2H), 1.7 (m, 2H), 1.2 (t, J=6.9 Hz, 9H), 0.62 (t, J=8.1 Hz, 2H).

Figure 2:
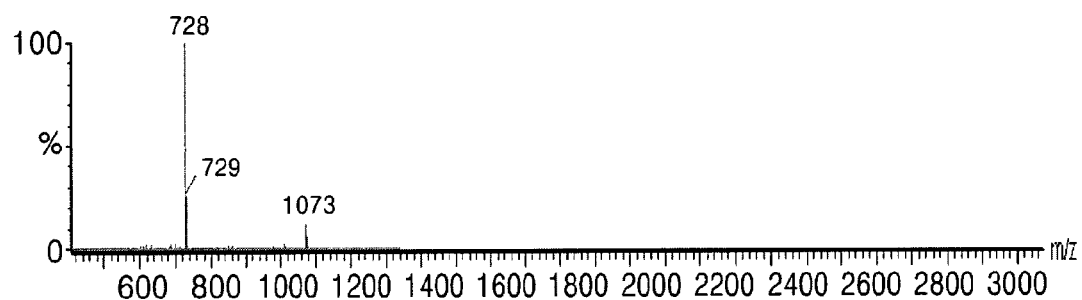
FIG. 2 is an ESI-Mass spectrum of succinic 2-{2-[2-(2-(3-triethoxysilylpropyl)-ethoxy)-ethoxy]-ethoxy}-ethyl ester 2,5-dioxo-pyrollidine-1-yl ester obtained from Example 2 of the present invention.

The ESI-Mass analysis result of the obtained compound (12) is illustrated in FIG. 2. The molecular weight of compound (12) was about 728.

Example 3

Producing of a Substrate Coated with Succinic 2-{2-[2-(2-(3-triethoxysilyl propyloxy)-ethoxy)-ethoxy]-ethoxy}-ethyl 2,5-dioxo-pyrollidine-1-yl ester (12) and Evaluation therefor 1. Producing of a Substrate Coated with Succinic 2-{2-[2-(2-(3-triethoxysilyl propyloxy)-ethoxy)-ethoxy]-ethoxy}-ethyl 2,5-dioxo-pyrollidine-1-yl ester (12)

Succinic 2-{2-[2-(2-(3-triethoxysilylpropyloxy)-ethoxy)-ethoxy]-ethoxy}-ethyl 2,5-dioxo-pyrollidine-1-yl ester (12) obtained in Example 2 was coated on a glass substrate using a self-assembling thin layer coating method. The coating procedure was as follows.

A solution of succinic 2-{2-[2-(2-(3-triethoxysilylpropyloxy)-ethoxy)-ethoxy]-ethoxy}-ethyl ester 2,5-dioxo-pyrollidine-1-yl ester (12) in ethanol (1% (wt/wt)) was coated using a self-assembling thin layer coating method. The self-assembled thin layer coating was carried out by immersing a cleansed glass in the coating solution for 1 hour. After the coating process was completed, the substrate was cleansed with ethanol for 5 minutes and the coating was hardened at 110° C. for 45 minutes. The hardened substrate was cleansed with an ethanol solution for 5 minutes to remove unreacted coating components remained on the surface of the substrate, and then was dried through spin dry.

2. Evaluation for Reactivity and Binding Force of Succinic 2-{2-[2-(2-(3-triethoxysilyl propyl)-ethoxy)-ethoxy]-ethoxy}-ethyl ester 2,5-dioxo-pyrollidine-1-yl ester (12)

(1) Reactivity and Binding Force to Alexa 532 Dye

Alexa 532 dye (Molecular Probe, USA) was immobilized on a substrate coated with succinic 2-{2-[2-(2-(3-triethoxysilylpropyl)-ethoxy)-ethoxy]-ethoxy}-ethyl ester 2,5-dioxo-pyrollidine-1-yl ester (12) prepared above 1. The immobilization was carried out by reacting a phosphate buffer saline (PBS) (0.1 M) solution containing the dye in a concentration of 100 µg/ml with the substrate at 37° C. for 1 hour.

The obtained substrate of the present invention was irradiated with light having a wavelength of 532 nm using a Genepix 4100B scanner (Axon, USA). The fluorescence emitted from the substrate was observed to determine the reactivity of the substrate. A substrate coated with an epoxy group (Telechem, SME, USA) and a substrate coated with an amino group (Corning, #40004, USA) as control groups were coated with the dye and the fluorescence intensity emitted from the substrates was measured.

Next, the substrates coated with the dye were, respectively, washed two times with a PBS (0.1 M) solution containing Tween 20 (0.5% (wt/wt)), and then the fluorescence intensity emitted therefrom was measured according to the same procedure as described above. The results are shown in Table 1.

TABLE 1

| Substrate | | Immediately after immobilization | After washing | Ratio of dye immobilized after washing (%) |
|---|---|---|---|---|
| Substrate of the present invention | Spot<br>Background | 20150<br>98 | 2530<br>82 | 13 |
| Substrate coated with epoxy group | Spot<br>Background | 15510<br>67 | 570<br>68 | 4 |
| Substrate coated with amino group | Spot<br>Background | 15086<br>112 | 352<br>108 | 2 |

As can be seen from Table 1, when using the substrate of the present invention, the ratio of the dye immobilized after washing is significantly high compared to the control substrates, which indicates that strong bonding between the compound and the dye is achieved.

(2) Reactivity and Binding Force to Insulin Having Alexa 532 Dye Bound Thereto

Insulin having Alexa 532 dye (Molecular Probe, USA) bound thereto was immobilized on a substrate coated with succinic 2-{2-[2-(2-(3-triethoxysilylpropyl)-ethoxy)-ethoxy]-ethoxy}-ethyl ester 2,5-dioxo-pyrollidine-1-yl ester (12) prepared above 1. The immobilization was carried out by reacting a PBS (0.1 M) solution containing the insulin in a concentration of 100 µg/ml with the substrate at 37° C. for 1 hour.

The obtained substrate of the present invention was irradiated with light having a wavelength of 532 nm using a Genepix 4100B scanner (Axon, USA). The fluorescence emitted from the substrate was observed to determine the reactivity of the substrate. A substrate coated with an epoxy group (Telechem, SME, USA) and a substrate coated with an amino group (Corning, #40004, USA) as control groups were coated with the insulin and the fluorescence intensity emitted from the substrates was measured.

Next, the substrates coated with the dye were, respectively, washed two times with a PBS (0.1 M) solution containing Tween 20 (0.5% (wt/wt)), and then the fluorescence intensity emitted therefrom was measured according to the same procedure as described above. The results are shown in Table 2.

TABLE 2

| Substrate | | Immediately after immobilization | After washing | Ratio of insulin immobilized after washing (%) |
|---|---|---|---|---|
| Substrate of the present invention | Spot<br>Background | 15511<br>41 | 7641<br>38 | 49 |
| Substrate coated with epoxy group | Spot<br>Background | 3708<br>37 | 366<br>39 | 10 |
| Substrate coated with amino group | Spot<br>Background | 7508<br>45 | 2026<br>53 | 27 |

As can be seen from Table 2, when using the substrate of the present invention, the ratio of the insulin immobilized after washing is significantly high compared to the control substrates, which indicates that strong bonding between the compound and the insulin is achieved.

(3) Effect on Specific Binding of Probe Material and Target Material

An anti-insulin antibody (Zymed Lab, clone z006) having Alexa 532 dye bound thereto were bound to the microarray with immobilized insulin produced above (2) to induce specific binding of insulin and anti-insulin antibody, and then fluorescence signals generated therefrom were measured.

First, in the microarray (25 spot/plate) with immobilized insulin produced above (2), insulin was mixed with a solution containing 100 ng/ml of anti-insulin antibody and they were reacted at 37° C. for 1 hour. Next, the resultant was washed two times with a PBS (0.1 M) solution containing Tween 20 (0.5% (wt/wt)).

Thereafter, the reactivity of the substrate of the present invention was determined by irradiating light having a wavelength of 532 nm to the substrate using a Genefix 4100B scanner (Axon, USA) and observing the fluorescence emitted therefrom at 550 nm. A substrate coated with an epoxy group (Telechem, SME, USA) and a substrate coated with an amino group (Corning, #40004, USA) as control groups were coated with the insulin and the fluorescence intensity emitted therefrom was measured. The results are shown in Table 3.

TABLE 3

| Substrate | | Fluorescence intensity | Ratio of fluorescence intensity of spot/background (%) |
|---|---|---|---|
| Substrate of the present invention | Spot<br>Background | 3125<br>89 | 35 |
| Substrate coated with epoxy group | Spot<br>Background | 853<br>62 | 14 |
| Substrate coated with amino group | Spot<br>Background | 1235<br>224 | 6 |

Figure 3:
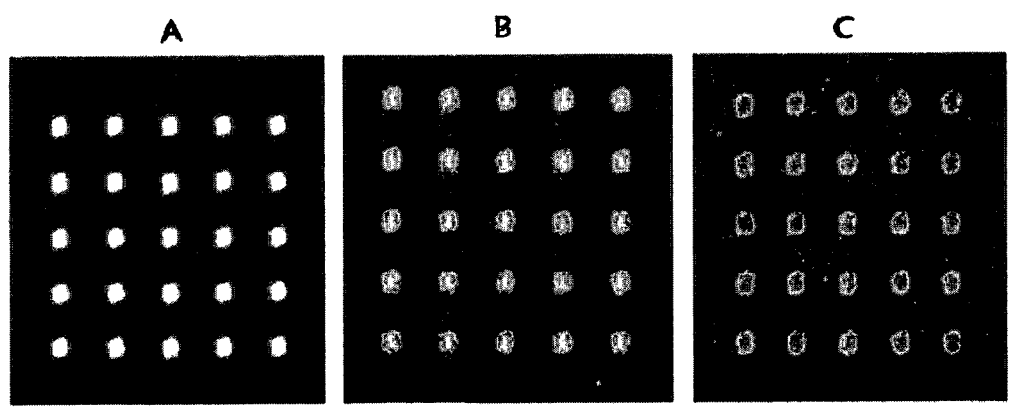
FIG. 3 illustrates fluorescence intensity and the shape of spots after a target material and a probe material are reacted on microarrays prepared using a substrate coated with a compound of the present invention, a substrate coated with an amino group and a substrate coated with an epoxy group.

As can be seen from Table 3, when using the microarray of the present invention, fluorescence signal having very high S/N ratio, i.e., very high fluorescence intensity of spot/background can be obtained. Also, as shown in FIG. 3, the spot shape of the substrate of the present invention is more distinct and clearer than the control substrates. In FIG. 3, A is the result for the microarray using the substrate of the present invention, B is the result for the microarray using the substrate coated with an amino group, and C is the result for the microarray using the substrate coated with an epoxy group.

It is assumed that the hydrophilicity of a microarray surface is varied according to the type of compound used as a linker and the difference in hydrophilicity influences signal generated from the reaction between a probe material and a target material. To prove this, the hydrophilicity of each microarray was identified by measuring a contact angle. The contact angle was measured using a contact angle meter (KRUSS GMBH, Germany). The results are shown in Table 4.

TABLE 4

| Substrate used in microarray | Contact angle |
|---|---|
| Substrate of the present invention | 15.1 |
| Epoxy substrate | 40 |
| Amino substrate | 60 |

As can be seen from Table 4, the microarray of the present invention has significantly high hydrophilicity compared to control groups.

According to the compound of the present invention, it includes all a portion capable of binding to a substrate, a hydrophilic portion and an activating portion, and thus can be used as a linker compound for immobilizing a probe material on a substrate.

According to the method of preparing the compound of the present invention, the compound of the present invention can be efficiently prepared.

According to the method of producing a microarray, a microarray having good signal generated from the reaction between a probe material and a target material can be produced.

According to the microarray of the present invention, the signal generated from the reaction between a probe material and a target material is good, and thus the microarray can be used in various analysis methods.

The substrate of the present invention has high reactivity and strong binding force to a probe material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of producing a microarray, the method comprising:
    coating a compound on a solid substrate, wherein the compound is represented by formula (4):

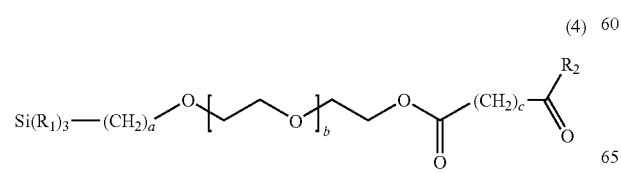

(4)

wherein each $R_1$ may be identical or different and is selected from a $C_1$-$C_2$ alkoxy group, a halogen and a formylalkyl group having a $C_1$-$C_3$ alkyl group, $R_2$ is

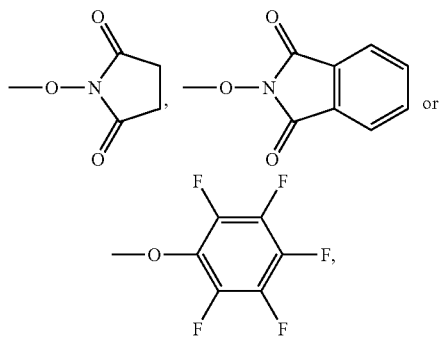

a is an integer from 3 to 18,
b is an integer from 1 to 200, and
c is an integer from 1 to 4; and
coupling the compound with a probe material to immobilize the probe material on the substrate.

2. The method of claim 1, wherein the coating is carried out using a method selected from the group consisting of a self-assembled thin-layer coating method, a spin coating method, a dipping method, a spraying method, a printing method and a Langmuir Blodget (LB) method.

3. A microarray produced using the method of claim 1.

4. The microarray of claim 3, which is a protein or polynucleotide microarray.

5. A method of producing a microarray, the method comprising:
    coating a compound on a solid substrate,
    wherein the compound is represented by formula (4):

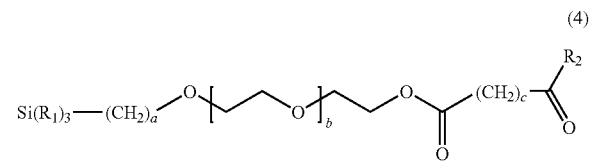

(4)

wherein $R_1$ is an ethoxy group,
$R_2$ is

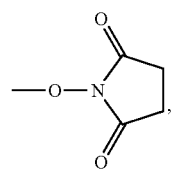

a is an integer from 3 to 18,
b is an integer from 1 to 200, and
c is 2 or 3; and
coupling the compound with a probe material to immobilize the probe material on the substrate.

6. The method of claim 5, wherein the coating is carried out using a method selected from the group consisting of a self-assembled thin-layer coating method, a spin coating method, a dipping method, a spraying method, a printing method and a Langmuir Blodget (LB) method.

7. A microarray produced using the method of claim 2.

8. A microarray produced using the method of claim 5.

9. A microarray produced using the method of claim 6.

10. The microarray of claim 7, which is a protein or polynucleotide microarray.

11. The microarray of claim 8, which is a protein or polynucleotide microarray.

12. The microarray of claim 9, which is a protein or polynucleotide microarray.

* * * * *